United States Patent
Shi et al.

(10) Patent No.: US 11,752,241 B2
(45) Date of Patent: Sep. 12, 2023

(54) BIOABSORBABLE STENT SYSTEM

(71) Applicant: BioVention LLC, El Monte, CA (US)

(72) Inventors: Chao Shi, Suzhou (CN); Yongwei Chien, Hong Kong (CN); Ella Liang, Claremont, CA (US); Zihang Yan, Woodland Hills, CA (US)

(73) Assignee: BioVention LLC, El Monte, CA (US)

( * ) Notice: Subject to any disclaimer, the term of this patent is extended or adjusted under 35 U.S.C. 154(b) by 35 days.

(21) Appl. No.: 16/945,492

(22) Filed: Jul. 31, 2020

(65) Prior Publication Data

US 2022/0001085 A1 Jan. 6, 2022

(30) Foreign Application Priority Data

Jul. 6, 2020 (CN) .......................... 202010639523.6

(51) Int. Cl.
*A61L 31/16* (2006.01)
*A61F 2/04* (2013.01)
(Continued)

(52) U.S. Cl.
CPC ................ *A61L 31/16* (2013.01); *A61F 2/04* (2013.01); *A61F 2/82* (2013.01); *A61F 2/958* (2013.01); *A61F 2/966* (2013.01); *A61K 35/28* (2013.01); *A61K 35/36* (2013.01); *A61K 35/44* (2013.01); *A61K 35/50* (2013.01); *A61L 31/022* (2013.01); *A61L 31/08* (2013.01); *A61L 31/148* (2013.01);
(Continued)

(58) Field of Classification Search
CPC ........ A61L 31/16; A61L 31/08; A61L 31/022; A61L 31/148; A61L 2300/30; A61F 2/966; A61F 2/82; A61F 2/04; A61F 2/958; A61F 2250/0039; A61F 2230/0067; A61F 2240/001; A61F 2210/0004; A61F 2230/0093; A61F 2/06; A61F 2250/0067; A61F 2230/0069; A61F 2002/041; A61K 35/36; A61K 35/50; A61K 35/28; A61K 35/44

See application file for complete search history.

(56) References Cited

U.S. PATENT DOCUMENTS 5,443,458 A 8/1995 Eury
5,605,696 A 2/1997 Eury et al.
(Continued)

FOREIGN PATENT DOCUMENTS

AU 2001259219 B2 6/2005

OTHER PUBLICATIONS

Koob et al., Biological properties of dehydrated human amnion/chorion composite graft: implications for chronic wound healing, International WOund Journal 2013; 10:493-500. (Year: 2013).*

*Primary Examiner* — Brian A Dukert
(74) *Attorney, Agent, or Firm* — Osha Bergman Watanabe & Burton LLP

(57) ABSTRACT

A bioabsorbable stent system may comprise one or more bioabsorbable stents and one or more restoration agents, wherein the one or more restoration agents are suitable for a targeting position and are coated on the surface of the bioabsorbable stent. A bioabsorbable stent system may comprise one or more bioabsorbable stents and one or more bioabsorbable films, wherein the bioabsorbable films are loaded with restoration agents and/or drugs suitable for a targeting position.

19 Claims, 15 Drawing Sheets

(51) Int. Cl.
  *A61F 2/82* (2013.01)
  *A61F 2/06* (2013.01)
  *A61F 2/958* (2013.01)
  *A61F 2/966* (2013.01)
  *A61K 35/28* (2015.01)
  *A61K 35/36* (2015.01)
  *A61K 35/44* (2015.01)
  *A61K 35/50* (2015.01)
  *A61L 31/02* (2006.01)
  *A61L 31/08* (2006.01)
  *A61L 31/14* (2006.01)

(52) U.S. Cl.
  CPC ........... *A61F 2/06* (2013.01); *A61F 2002/041* (2013.01); *A61F 2210/0004* (2013.01); *A61F 2230/0067* (2013.01); *A61F 2230/0069* (2013.01); *A61F 2230/0093* (2013.01); *A61F 2240/001* (2013.01); *A61F 2250/0039* (2013.01); *A61F 2250/0067* (2013.01); *A61L 2300/30* (2013.01)

(56) References Cited

U.S. PATENT DOCUMENTS

| | | |
|---|---|---|
| 5,629,077 A | 5/1997 | Turnlund et al. |
| 5,637,113 A | 6/1997 | Tartaglia et al. |
| 5,980,564 A | 11/1999 | Stinson |
| 6,251,136 B1 | 6/2001 | Guruwaiya et al. |
| 6,497,729 B1 | 12/2002 | Moussy et al. |
| 6,838,528 B2 | 1/2005 | Zhao |
| 6,897,205 B2 | 5/2005 | Beckert et al. |
| 7,056,338 B2 | 6/2006 | Shanley et al. |
| 7,169,187 B2 | 1/2007 | Datta et al. |
| 7,842,737 B2 | 11/2010 | Wang et al. |
| 8,016,874 B2 | 9/2011 | Casey |
| 8,034,048 B2 | 10/2011 | Pugsley et al. |
| 8,089,029 B2 | 1/2012 | Flanagan |
| 9,205,177 B2 * | 12/2015 | Schorgl .................... A61F 2/07 |
| 9,333,099 B2 | 5/2016 | Pacetti et al. |
| 9,522,217 B2 | 12/2016 | Kutryk et al. |
| 2004/0106945 A1 * | 6/2004 | Thramann ................ A61F 2/95 606/200 |
| 2007/0043426 A1 | 2/2007 | Abbate |
| 2007/0254012 A1 | 11/2007 | Ludwig et al. |
| 2008/0103583 A1 | 5/2008 | Dutta |
| 2008/0167682 A1 | 7/2008 | Corcoran et al. |
| 2015/0265438 A1 * | 9/2015 | Hossainy ................. A61F 2/89 623/1.11 |
| 2017/0281832 A1 * | 10/2017 | Ramzipoor ............. A61L 31/04 |
| 2018/0042738 A1 * | 2/2018 | Sun ........................ A61L 31/06 |
| 2021/0030571 A1 * | 2/2021 | Miao ..................... A61L 31/129 |

* cited by examiner

BIOABSORBABLE STENT SYSTEM

FIELD

The present disclosure relates to stents, and in particular to vascular, biliary, otolaryngology, urogenital, respiratory, alimentary and neural stents that made of biodegradable materials which improves efficacy and safety via degradation, erosion and absorption with or without pharmaceutical applications.

The stent may also contain drug or other biological agents for the treatment and restoration of arthrosclerosis disease, vessel inflammation or prevention of thrombosis and stenosis formation.

BACKGROUND

Stent procedures are fairly common, and various types of stents have been developed and used. Several types of these endoprostheses are known, including balloon expandable, self-expanding, and endoprostheses constructed from biostable springs or tubes. Stent is used not only as a mechanical intervention in body conduits but also as a vehicle for providing medical therapy. As a mechanical intervention, stent acts as stentings, functioning to physically hold open and, if desired, to expand the wall of the passageway. As a vehicle for providing medical therapy, stent releases relevant drugs to treat certain disease. It has been widely used in medical devices field to use bioabsorbable stent system to treat relevant diseases. Among all these applications, coronary stent technology has the longest application history. Nowadays, there are many branch studies and applications on other body parts such as natural and human-made body chamber or conduits.

After years of clinical application and research experience, current bioabsorbable stent has the following insufficiencies during usage:

1. Some patients may be allergic to some drug loaded bioabsorbable stents.

2. Some bioabsorbable stents have low radial strength after expansion, especially stents made of plastics.

3. Some plastic stents cannot be well crimped on delivery system such as balloon catheters.

4. Stent implantation is not often regarded as the first option while treating. Interventional therapy is often used before stent implantation. However, restenosis often occurs after stent absorption or stent removal especially in cases repeating interventional surgeries have been conducted. Cicatricial tissue is easy to form after repeating irritation which in return causes restenosis.

SUMMARY

A medical stent system is provided that treats disease and then restores affected tissue.

A bioabsorbable stent system is composed of bioabsorbable stent(s), restoration agents, and delivery system. The bioabsorbable stent may be made of bioabsorbable materials. The restoration agent, integrated with the bioabsorbable stent may be used to restore the targeted tissues. The delivery system may be designed for delivering and expanding if necessary, the bioabsorbable stent(s) and restoration agents.

In one or more embodiments, the bioabsorbable stent may be coated with restoration agent and/or drugs.

In one or more embodiments, the bioabsorbable stent system may comprise bioabsorbable film(s) that the restoration agent and/or drugs are loaded in bioabsorbable film(s) and at least one layer of the bioabsorbable film will coaxially connect the surface of the bioabsorbable stent.

In one or more embodiments, the first layer of coating loaded with restoration agent on the surface of the bioabsorbable stent may be sandwiched between the bioabsorbable stent and the second layer of coating loaded with drugs.

In one or more embodiments, the first layer of the bioabsorbable film loaded with restoration agent may be sandwiched between the bioabsorbable stent and the second layer of the bioabsorbable film loaded with drugs.

In one or more embodiments, the bioabsorbable stent system may comprise multiple coaxial bioabsorbable stents and the bioabsorbable film which is loaded with restoration agents and is sandwiched between two adjacent bioabsorbable stents.

In one or more embodiments, the bioabsorbable stent may be naked and or coated with restoration agents and/or drugs.

In one or more embodiments, the bioabsorbable stent system may comprise the first layer of the bioabsorbable stent which is naked or coated with restoration agents, and the second layer of the bioabsorbable stent which is naked stent or coated with drugs. The second layer of the bioabsorbable stent is coaxial on the outside of the first layer of the bioabsorbable stent.

In one or more embodiments, the bioabsorbable stent system comprises the first layer of the bioabsorbable stent, the first layer of the bioabsorbable film, the second layer of bioabsorbable film and the second layer of the bioabsorbable stent from the inside out.

In one or more embodiments, the second layer of the bioabsorbable film is amniotic membrane, and the first layer of the bioabsorbable film is loaded with stem cells and its carrier, epithelial cells and its carrier, endothelial cells and its carrier and/or cell growth factors.

In one or more embodiments, the bioabsorbable stent system comprises the first layer of the bioabsorbable stent, the first layer of the bioabsorbable film, the second layer of bioabsorbable stent, the second layer of the bioabsorbable film and the third layer of the bioabsorbable stent from the inside out.

In one or more embodiments, the bioabsorbable film comprises one or more kinds of amniotic membrane and film containing restoration agents. The restoration agents comprise one or more kinds of cell growth factors and stem cells and its carrier, epithelial cells and its carrier, endothelial cells and its carrier.

In one or more embodiments, the bioabsorbable film is made of one kind or a mixture of bioabsorbable materials including but not limited to poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly (glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. The film has elasticity and is very flexible since it is made of plastics.

In one or more embodiments, the cell carrier is comprised of culture medium, a protein, peptide, or antibody that cultivates and attracts and binds stem, endothelial or epithelial cells.

In one or more embodiments, the restoration agents comprise one or more kinds of stem cells and its carrier, epithelial cells and its carrier, endothelial cells and its carrier, cell growth factors and amniotic membrane.

In one or more embodiments, the bioabsorbable stent is made of one kind or a mixture of bioabsorbable materials including but not limited to magnesium or magnesium alloys, zinc alloy, iron, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

The bioabsorbable stent may be manufactured by cutting, weaving, casting, molding, welding, and/or adhesive bonding.

In one or more embodiments, the coating on the surface of the bioabsorbable stent may be made of one kind or a mixture of bioabsorbable materials including but not limited to poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

In one or more embodiments, the bioabsorbable film may be physically crimped and sandwiched by two adjacent bioabsorbable stents.

In one or more embodiments, the bioabsorbable stent(s) and bioabsorbable film(s) may be overlapped and jointed together through suturing, welding, co-molding, co-extrusion, adhesive bonding, solvent bonding.

If a drug is coated on the stent, the drug should fit the need of treating in implantation site.

In one or more embodiments, the shape of the bioabsorbable stent after expansion is irregular or regular such as cylindrical, conical, frustum, umbrella.

In one or more embodiments, when the shape of the bioabsorbable stent is frustum, the diameter of proximal stent is smaller than that of the distal stent.

The dimension of the bioabsorbable stent may be designed to enter and fit implantation position of body conduits.

The bioabsorbable stent and film may be porous or not depending on clinical needs.

Cell growth factors or restoration cells alone have sort of cell restoration effect. Combining cell growth factors and restoration cells may be more powerful and effective.

In one or more embodiments, cell growth factors may be obtained from any of animal and plant extraction and artificial synthesis including but not limited to platelet-related growth factors (PDGF, ODGF), epidermal growth factors (EGF, TGFα and TGFβ), fibroblast growth factor (αFGF, βFGF), insulin-like growth factor (IGF-I, IGF-II), nerve growth factor (NGF), interleukin growth factors (IL-1, IL-1, IL-3, etc.), erythropoietin (EPO), colony stimulating factor (CSF).

In one or more embodiments, the drugs used may comprise one or more of antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti-parkinson agents, thyroid therapeutic agents, spasmolytics, platelet aggregation inhibitors, vitamins, cytostatics ametastasis inhibitors, phytopharmaceuticals, chemotherapeutic agents and amino acids.

The delivery system is designed to accommodate self-expanding and non-self-expanding stent system and deliver the bioabsorbable stent and restoration agents to target position.

The delivery system is composed of hollowing tubing, push rod, handler and stent compressor, which may be used to deliver the self-expanding stent system. For non-self-expanding stent system, the delivery system may be a commonly used balloon catheter. The shape of the balloon catheter is circular or frustum or any shape suitable to fit the implantation site. The bioabsorbable stent(s) and the restoration agents will be crimped on the balloon catheter before implanting.

The bioabsorbable stent system according to some embodiments may treat disease first with bioabsorbable stent or a bioabsorbable film with or without drugs and then may use the restoration agents to restore the affected and treated tissues. According to some embodiments, using multiple bioabsorbable stents and restoration agents, the degradation rate, sequence of complete degradation of bioabsorbable stents and restoration agents, and the category of cell growth factors and drugs and cells may be designed according to relevant clinical need, so the customized and precise treatment and restoration therapy may be realized. The bioabsorbable film may also act as a buffer sandwiched between two crimped coaxial bioabsorbable stents which may prevent the tangle and interference of stents from each other.

DETAILED DESCRIPTION

Figure 1:
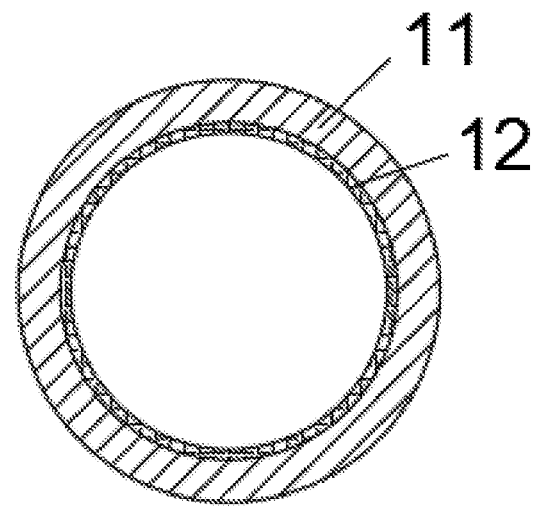
FIG. 1 shows an illustration of the cross section of bioabsorbable stent system in Example 1.

The following examples are described in combination with the appended drawings, so that the advantages and characteristics of the present disclosure can be easy to understand. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant disclosure.

Although only some embodiments are described in detail herein, those skilled in the art will readily appreciate that many modifications, permutations, combinations, and variations are possible thereof. Accordingly, all such modifications, permutations, combinations, and variations are intended to be included within the scope of this disclosure as defined in the following claims.

Definitions

"Polymer" as used herein, refers to a series of repeating monomelic units that have been cross-linked or polymerized. Any suitable polymer can be used to carry out the present disclosure. It is possible that the polymers of the disclosure may also comprise two, three, four or more different polymers. In some embodiments, of the disclosure only one polymer is used.

In some embodiments a combination of two polymers are used. Combinations of polymers can be in varying ratios, to provide coatings with differing properties. Those of skill in the art of polymer chemistry will be familiar with the different properties of polymeric compounds.

"Bioabsorbable" refers to polymers that are capable of being completely eroded or absorbed when exposed to bodily fluids such as blood and can be gradually resorbed, absorbed, and/or eliminated by the body.

"Biodegradable" A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration is typically in the range of six to eighteen months.

"Solvent" is defined as an active agents capable of dissolving or dispersing one or more other active agents or capable of at least partially dissolving or dispersing the active agents(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

"Drug or therapeutic agents" as used herein refer to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Examples of therapeutic agents employed in conjunction with the disclosure include but not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti-parkinson agents, thyroid therapeutic agents, spasmolytics, platelet aggregation inhibitors, vitamins, cytostatics ametastasis inhibitors, phytopharmaceuticals, chemotherapeutic agents and amino acids. It is possible that the pharmaceutical agents of the disclosure may also comprise two or more drugs or pharmaceutical compounds.

"Active ingredients" may be acarbose, antigens, beta-receptor blockers, non-steroidal antiinflammatory drugs (NSAIDs), cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, sahneterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, Zolpidem, zoplicone, zotipine and the like. See, e.g., U.S. Pat. No. 6,897,205; see also U.S. Pat. Nos. 6,838,528; 6,497,729.

"Delivery" refers to introducing and transporting the stent through a bodily lumen to a region, such as a lesion, in a vessel that requires treatment.

"Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

"Restoration" refers to complex biological process of repair and regeneration of injured tissues or vessels thru neo endothelization or epithelization using therapeutic or pharmaceutic agents.

The design of the bioabsorbable stent system is to treat disease first with bioabsorbable stent or a bioabsorbable film with or without drugs and then use the restoration agents to restore the affected and treated tissues. The delivery system may be designed to accommodate self-expanding and non-self-expanding stent system and deliver the bioabsorbable stent and restoration agents to target position. The delivery system is composed of hollowing tubing, push rod, handler and stent compressor which is used to deliver the self-expanding stent system. The bioabsorbable stent system is firstly compressed by the stent compressor and then loaded in the distal tip of the hollowing tubing. Deliver the hollowing tubing to the target position and push out to release the bioabsorbable stent(s) and the restoration agents by using the pushing rod. Extract the hollowing tubing. The bioabsorbable stent(s) and the restoration agents expand themselves and are positioned on the target position. For non-self-expanding stent system, the delivery system is a commonly used balloon catheter. The delivery system is a commonly used balloon catheter. The bioabsorbable stent(s) and the restoration agents are crimped on the balloon first. Deliver the balloon catheter to the target position and inflate the balloon. The bioabsorbable stent(s) and the restoration agents are expanded accordingly. Deflate the balloon and extract and retreat the balloon catheter. The bioabsorbable stent(s) and the restoration agents are positioned on the target position. The shape of the balloon catheter is circular or frustum or shape fits implantation site so does the shape of the bioabsorbable stent(s) system.

The bioabsorbable stent is made of one kind or a mixture of bioabsorbable materials including but not limited to magnesium or magnesium alloys, zinc alloy, iron, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. The shape of the bioabsorbable stent after expansion is irregular or regular such as cylindrical, conical, frustum, umbrella. When the shape of the bioabsorbable stent is frustum, the diameter of proximal end is smaller than that of the distal end. The dimension of the bioabsorbable stent is properly designed to enter and fit body chamber. The bioabsorbable stent and film can be porous or not depending on clinical needs. The bioabsorbable stent can be manufactured by cutting, weaving, casting, molding, welding, adhesive bonding.

Restoration agents include one kind or a mixture of amniotic membrane, cell growth factors, stem cells and its carrier, epithelial cells and its carrier, endothelial cells and its carrier. Cell growth factors can be obtained from animal and plant extraction and artificial synthesis including but not limited to platelet-related growth factors (PDGF, ODGF), epidermal growth factors (EGF, TGFα and TGFβ), fibroblast growth factor (αFGF, βFGF), insulin-like growth factor (IGF-I, IGF-II), nerve growth factor (NGF), interleukin growth factors (IL-1, IL-1, IL-3, etc.), erythropoietin (EPO), colony stimulating factor (CSF).

Restoration agents and drugs can be in the form of coating on the surface of the bioabsorbable stent and bioabsorbable film integrated with the bioabsorbable stent.

For example, when in the form of coating, the restoration agents with or without drugs will be mixed together in a polymer solution and sprayed on the surface of the bioabsorbable stent. For example, mixing one or more kinds of cell growth factors and drugs in a polymer solution and then spray it on the surface of the bioabsorbable stent. The restoration agents with or without drugs can also be implanted on the stent by immersion in the restoration agents solution or by brushing. The coating is made of one kind or a mixture of bioabsorbable materials including but not limited to poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

For example, when in the form of the bioabsorbable film, the whole film of amniotic membrane alone are the restoration agents. The bioabsorbable film can also contain one kind or a mixture of cell growth factors and/or cells and its carrier loaded in bioabsorbable plastics such as stem cells and its carrier, epithelial cells and its carrier, endothelial cells and its carrier. The carrier is comprised of culture medium, a protein, peptide, or antibody that cultivates and attracts and binds stem, endothelial or epithelial cells. The bioabsorbable film is made of one kind or a mixture of bioabsorbable materials including but not limited to poly (N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrateco-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. The bioabsorbable film has elasticity and is very flexible since it is made of plastics. The bioabsorbable film is porous or not depending on clinical needs.

Cell growth factors or cell and its carrier alone can act as restoration agents, which release cell growth factors or cells to restore tissues. The bioabsorbable film can also contain cell growth factors and cell and its carrier at the same time. Cell growth factors or restoration cells alone have sort of cell restoration effect. It is more powerful and effective to combine cell growth factors and restoration cells.

One kind or a mixture of drugs are loaded in the bioabsorbable stent system include but are not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti-parkinson agents, thyroid therapeutic agents, spasmolytics, platelet aggregation inhibitors, vitamins, cytostatics ametastasis inhibitors, phytopharmaceuticals, chemotherapeutic agents and amino acids. The drug should fit the need of treating in implantation site if drug is used.

The bioabsorbable stent system can comprise one or more bioabsorbable stents to enhance the radial force. The bioabsorbable stent is naked or coated with restoration agents and/or drugs. When multiple bioabsorbable stents are employed, coaxial bioabsorbable stents and one or more bioabsorbable film(s) which is loaded with restoration agents and/or drugs and is sandwiched between two adjacent bioabsorbable stents. In this multiple bioabsorbable stents and restoration agents design, the degradation rate, sequence of complete degradation of bioabsorbable stents and restoration agents, and the category of cell growth factors and drugs and cells can be designed according to relevant clinical need, so the customized and precise treatment and restoration therapy can be realized. The bioabsorbable film can also act as the buffer sandwiched between two crimped coaxial bioabsorbable stents which can prevent the tangle and interference of stents from each other.

The bioabsorbable film is physically crimped and sandwiched by two adjacent bioabsorbable stents. The bioabsorbable stent(s) and bioabsorbable film(s) are also overlapped and jointed together through suturing, welding, co-molding, co-extrusion, adhesive bonding, solvent bonding. For the bioabsorbable stent system that contains multiple bioabsorbable stents, the outside layer of bioabsorbable stent, coated with drug or not, is designed to treat certain disease. The restoration agents loaded in the inside layer of bioabsorbable film such as cell growth factors or cell and its carrier will restore the tissues. The outside layer of bioabsorbable stent is naked if the bioabsorbable stent is fast degradable magnesium. The outside layer of bioabsorbable stent can also be coated with drugs alone or together with cell growth factors which can release drugs to treat and restoration agents to restore tissues at the same time.

Example 1

FIG. 1 illustrates an example of the structure of the bioabsorbable stent system which comprises one bioabsorbable stent and one bioabsorbable film before compression or crimping. The bioabsorbable stent 11 coated with drug will release drugs to treat and gradually degrade or be endothelialized. For some applications where no drug is needed for treating, the bioabsorbable stent 11 is naked. The bioabsorbable film 12 containing one kind or a mixture of cell growth factors or cell and its carrier will release cell growth factors or epithelial or stem cells to restore the affected and treated tissues.

Example 2

Figure 2:
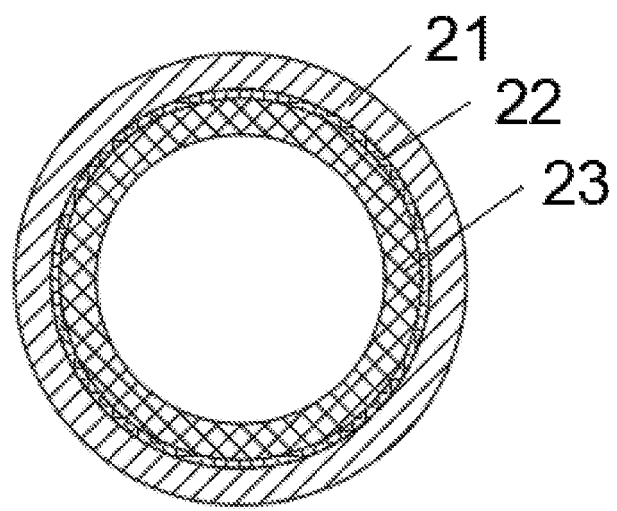
FIG. 2 shows an illustration of the cross section of bioabsorbable stent system in Example 2.

FIG. 2 shows an example of the structure of the bioabsorbable stent system which comprises two bioabsorbable stents and one bioabsorbable film before compression or crimping. The second layer of bioabsorbable stent 21, the first layer of bioabsorbable stent 23 and the bioabsorbable film 22 are shown in FIG. 2. This structure of two stents can enhance the overall radial strength. The bioabsorbable stent 21 has restrictions on the bioabsorbable stent 23 which makes it possible to crimp some hard-to-crimp bioabsorbable stent 23. The bioabsorbable film 22 is a whole amniotic membrane film or a film containing cell growth factors or a film containing stem cells and its carrier, epithelial cells and its carrier, endothelial cells and its carrier or a film containing a mixture of cell growth factors and cells such as stem cells and its carrier, epithelial cells and its carrier, endothelial cells and its carrier. The bioabsorbable film 22 can also act as the buffer sandwiched between two crimped coaxial bioabsorbable stent 21 and 23 which can prevent the tangle and interference of stents from each other. The bioabsorbable stent 21 is coated with drug or is made of fast degrade magnesium or alloy. The bioabsorbable stent 23 is naked or coated with one kind or kinds of cell growth factors. Particularly, when the bioabsorbable stent 21 is made of naked degrade magnesium or alloy, the fast degradation makes the tissues locally alkaline which can take the microbes and adhesive and hyperplasia tissues down. This special cure design of treating fits these patients who are allergic to certain drugs.

Example 3

Figure 3:
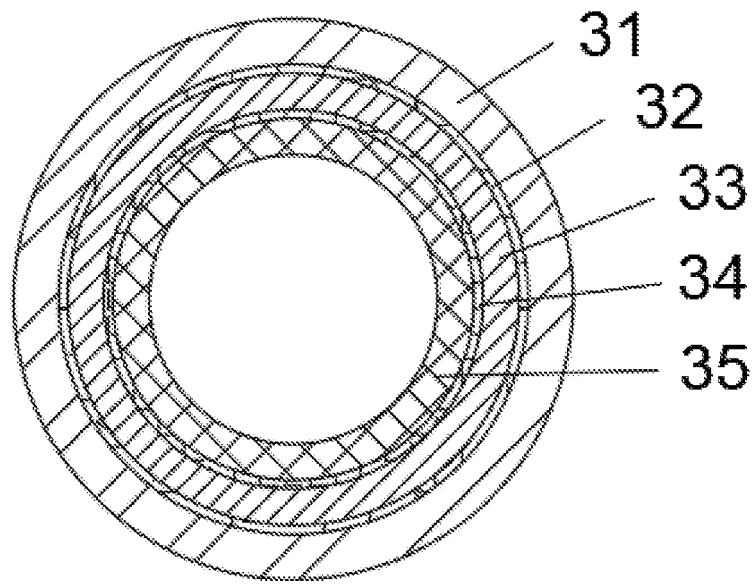
FIG. 3 shows an illustration of the cross section of bioabsorbable stent system in Example 3.

FIG. 3 depicts an example of the structure of the bioabsorbable stent system which comprises three bioabsorbable stents and two bioabsorbable films before compression or crimping. The first layer of bioabsorbable stent 35, the second layer of bioabsorbable stent 33 and the third layer of bioabsorbable stent 31 are naked or coated with drugs or cell growth factors. The first layer of bioabsorbable film 34 and the second layer of bioabsorbable film 32 can release cells or cell growth factors and act as the buffer sandwiched between two coaxial stents. The third layer of bioabsorbable stent 31 has restrictions on the first layer of bioabsorbable stent 35 and the second layer of bioabsorbable stent 33, which makes it possible to crimp some hard-to-crimp bioabsorbable stent 33 or 35. This multiple stents design can substantially enhance the overall radial strength and especially fit the application where very strong radial support is needed. In this multiple bioabsorbable stents and bioabsorbable films design, the degradation rate, sequence of complete degradation of bioabsorbable stents and bioabsorbable film, and the category of cell growth factors and drugs and cells can be designed according to relevant clinical need. So the customized and precise therapy of multiple and repeating treatment and restoration can be realized.

Example 4

Figure 4:
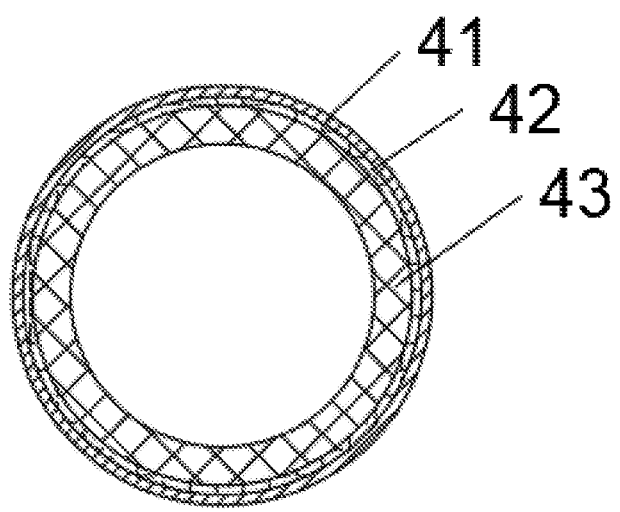
FIG. 4 shows an illustration of the cross section of bioabsorbable stent system in Example 4.

FIG. 4 describes an example of the structure of the bioabsorbable stent system which comprises one bioabsorbable stent and two bioabsorbable films before compression or crimping. The second layer of bioabsorbable film 41 is a drug coated film that releases drugs to treat. The first layer of bioabsorbable film 42 is a whole amniotic membrane film or a film containing cell growth factors or a film containing stem cells and its carrier, epithelial cells and its carrier, endothelial cells and its carrier or a film containing a mixture of cell growth factors and cells such as stem cells and its carrier, epithelial cells and its carrier, endothelial cells and its carrier. The first layer of bioabsorbable film 42 releases cell growth factors or cells or both to restore affected and treated tissues. The bioabsorbable stent 43 is naked or coated with cell growth factors and acts as the backbone to support the whole system.

Example 5

Figure 5:
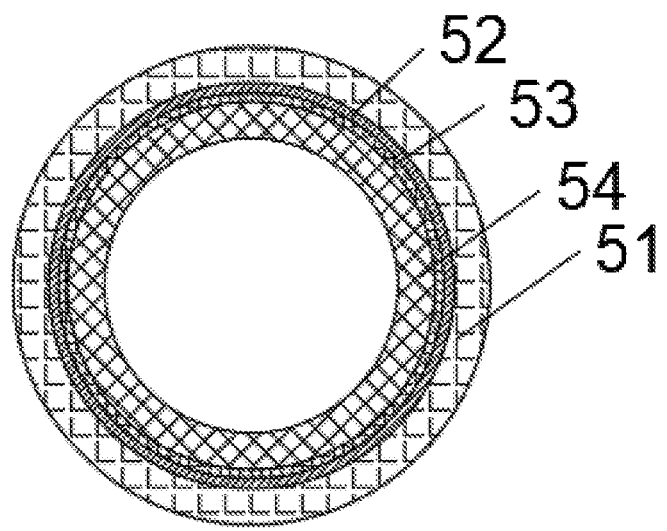
FIG. 5 shows an illustration of the cross section of bioabsorbable stent system in Example 5.

FIG. 5 illustrates an example of the structure of the bioabsorbable stent system which comprises two bioabsorbable stents and two bioabsorbable films before compression or crimping. The second layer of bioabsorbable stent 51 is naked or coated with drugs and the first layer of bioabsorbable stent 54 is naked or coated with one or kinds of cell growth factors. The second layer of bioabsorbable film 52 is a whole amniotic membrane. The first layer of bioabsorbable film 53 is a film containing cell growth factors or cells or both to restore affected and treated tissues. Cell growth factors or restoration cells alone have sort of cell restoration effect. It is more powerful and effective to combine cell growth factors and restoration cells.

Example 6

Figure 6:
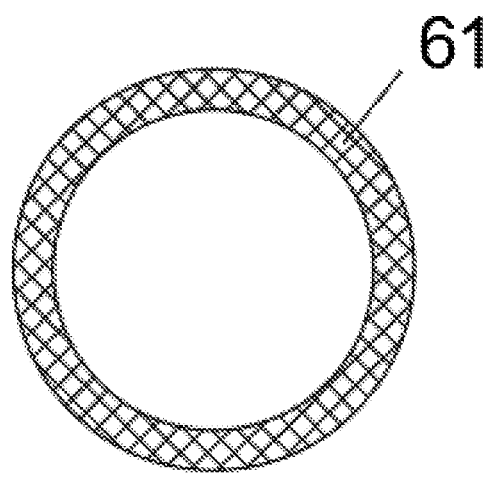
FIG. 6 shows an illustration of the cross section of bioabsorbable stent system in Example 6.

FIG. 6 depicts an example of the structure of the bioabsorbable stent system which comprises one bioabsorbable stent alone before compression or crimping. The bioabsorbable stent 61 is coated with drugs and cell growth factors. No additional bioabsorbable film is needed. The bioabsorbable stent 61 can release drugs and cell growth factors at the same time by spraying drugs and cell growth factors on the surface of the bioabsorbable stent 61 at the same time. Thus treating and restoring the tissues at the same time can be achieved. The bioabsorbable stent 61 can also be designed to release drugs first and then cell growth factors after the drug coating degrades by spraying or immersing the cell growth factors coating first and then the drug coating. Thus therapy of treating first and restoring second can be achieved.

Figure 7A:
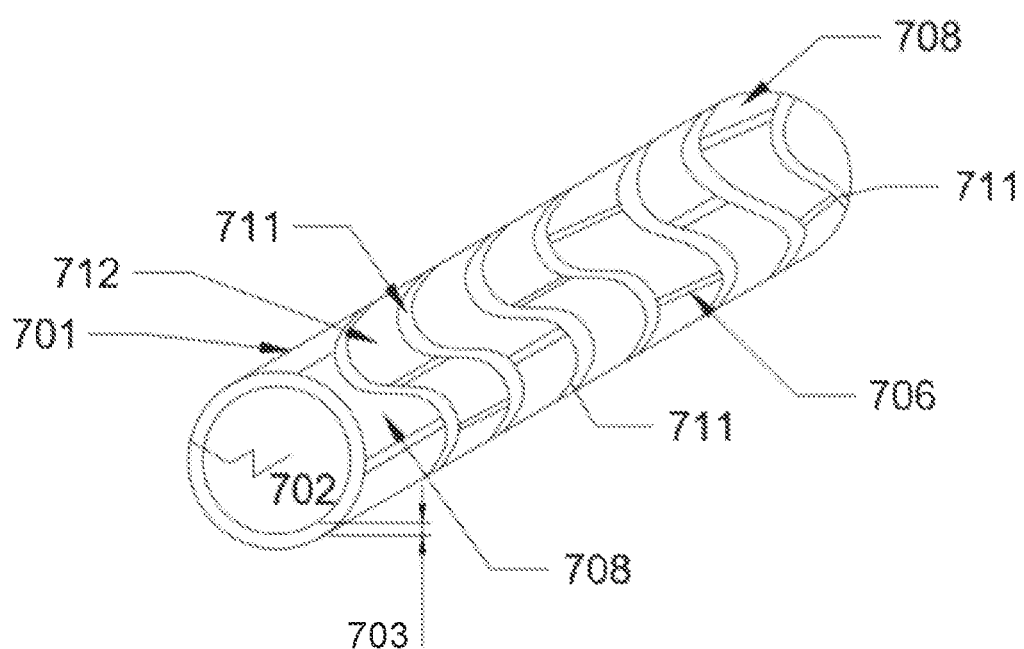
FIGS. 7A-B show a structure illustration of the bioabsorbable stent system.
Figure 7B:
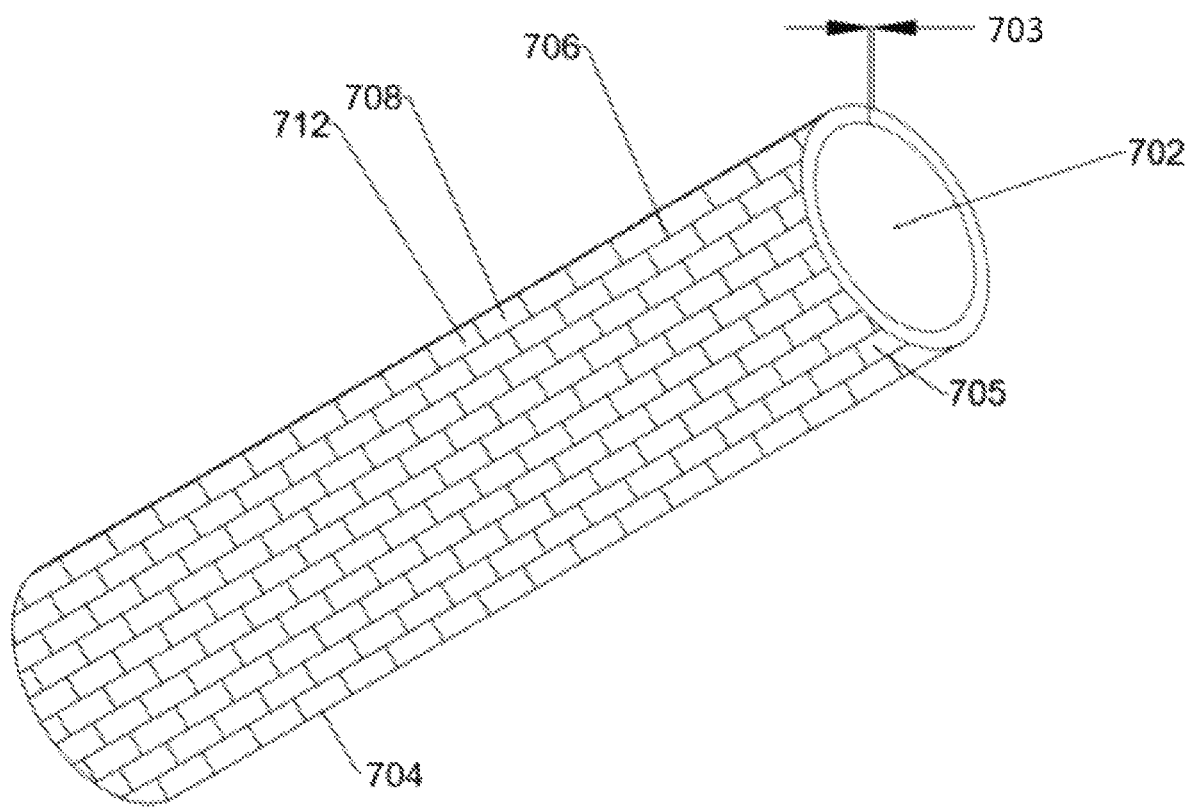
Figure 7C:
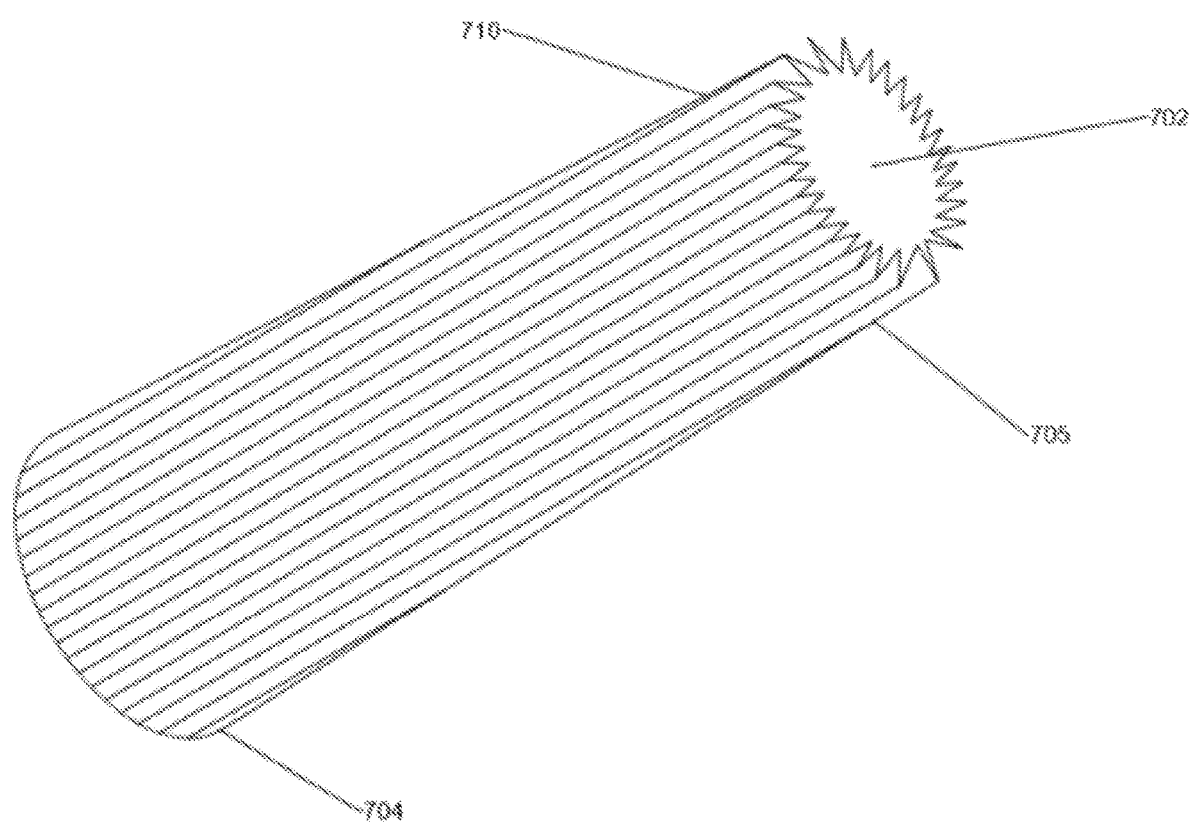
FIG. 7C is a structure illustration of the bioabsorbable stent or film after crimping or compressing.
Figure 7D:
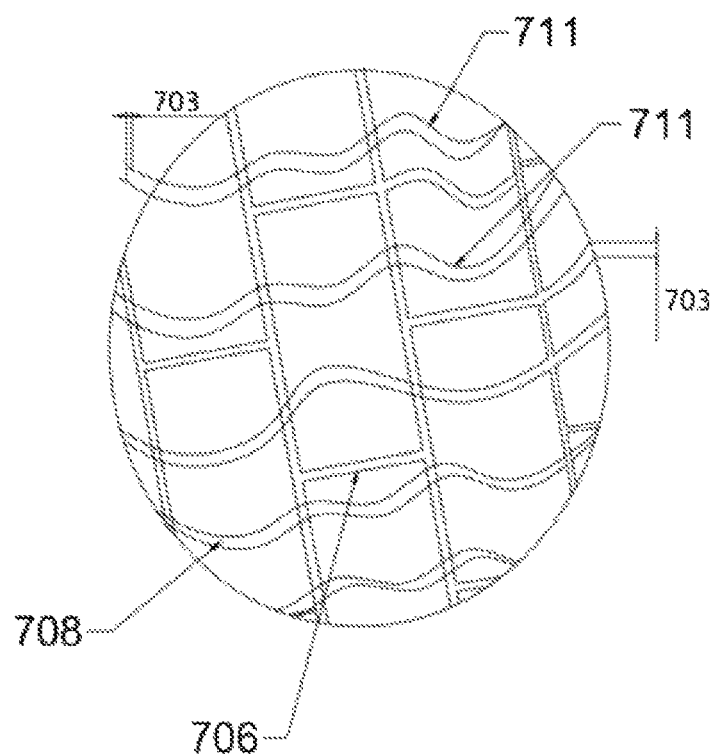
FIG. 7D is an illustration of partial enlarged detail of the bioabsorbable stent system.
Figure 7E:
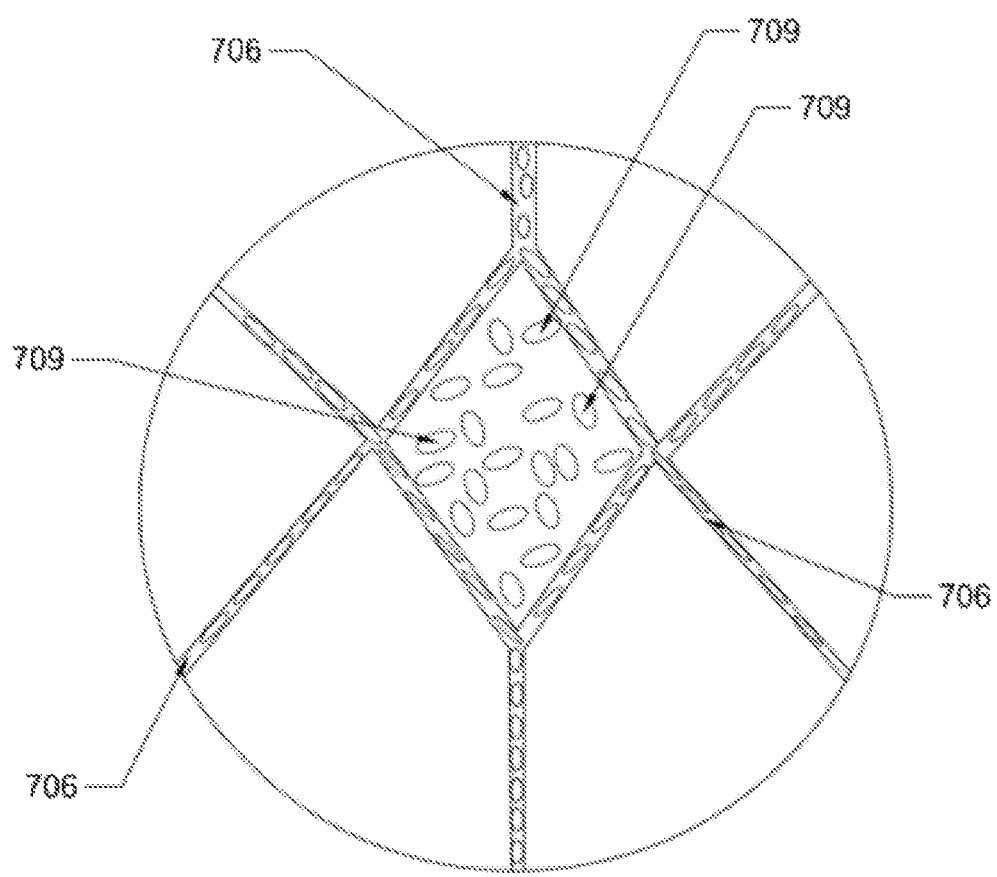
FIG. 7E is an illustration of partial enlarged detail of the bioabsorbable stent coating.

FIGS. 7A-E illustrate the detached structure of the bioabsorbable stent system. In FIG. 7A, the tube can be laser cut or cast to form a porous bioabsorbable stent that includes a pattern of a plurality of interconnecting link 706 and structural elements or struts 711 which form rings. The bioabsorbable stent can be radially compressed (crimped) and radially expanded. The diameter of the distal end 705 and proximal end 704 of the bioabsorbable stent may be the same or different after expansion. The strut 711, link 706, the outer surface 701 and inner surface 702 of the stent together form an open cell hole 708. The bioabsorbable stent has wall thickness 703. There is the chamber 712 between two adjacent open cell holes 708 as shown in FIG. 7A and FIG. 7B. FIG. 7C depicts the structure of the bioabsorbable stent or bioabsorbable film 710 with film thickness 707 after crimping or compressing. FIG. 7D depicts partial enlarged detail of a bioabsorbable stent open cell hole 708. The chamber 712 and open cell holes 708 include portions of struts 711 that are straight or relatively straight as described in FIG. 7E. The embodiments are easily applicable to other patterns and other devices. The variations in the structure of patterns are virtually unlimited. Drugs or cell growth factors 709 are dispersed on the surface of the bioabsorbable stent.

Figure 8:
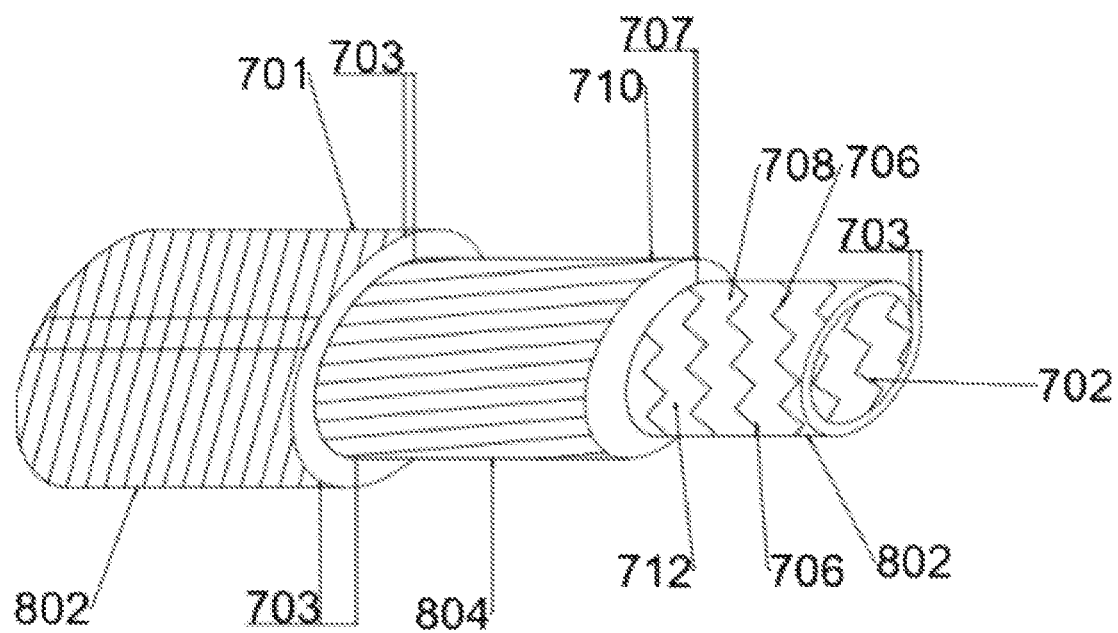
FIG. 8 is a structure illustration of the bioabsorbable stent system.
Figure 9A:
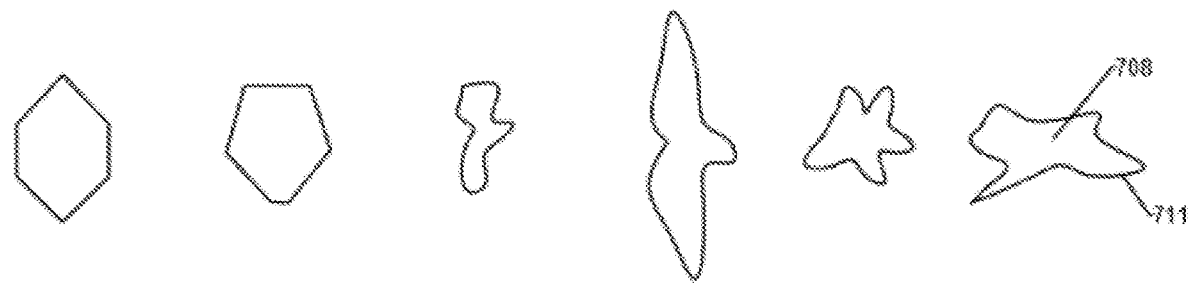
FIGS. 9A-E show an illustration of unit pattern of the bioabsorbable stent.
Figure 9B:
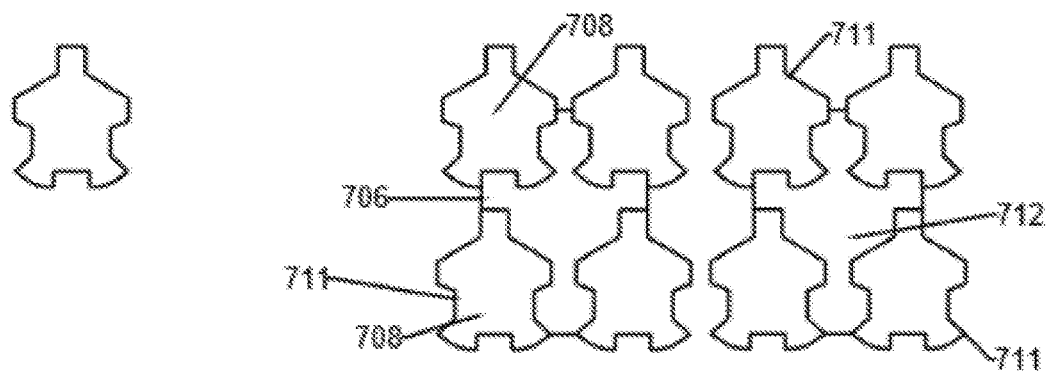
Figure 9C:
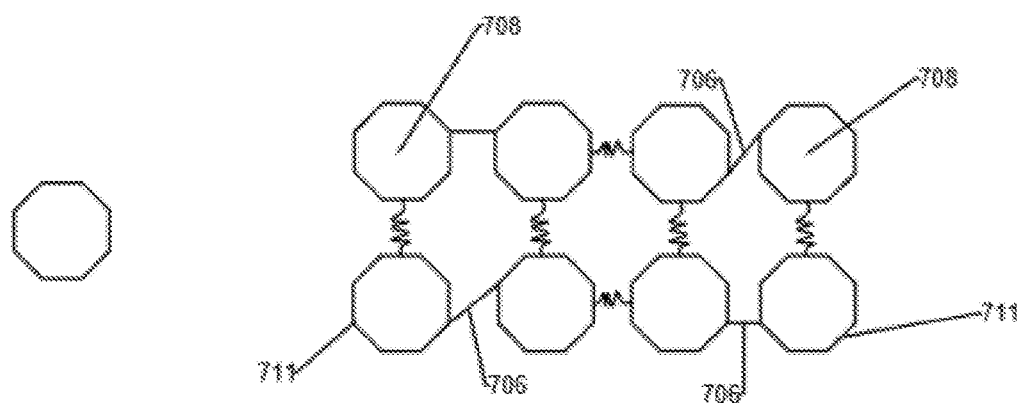
Figure 9D:
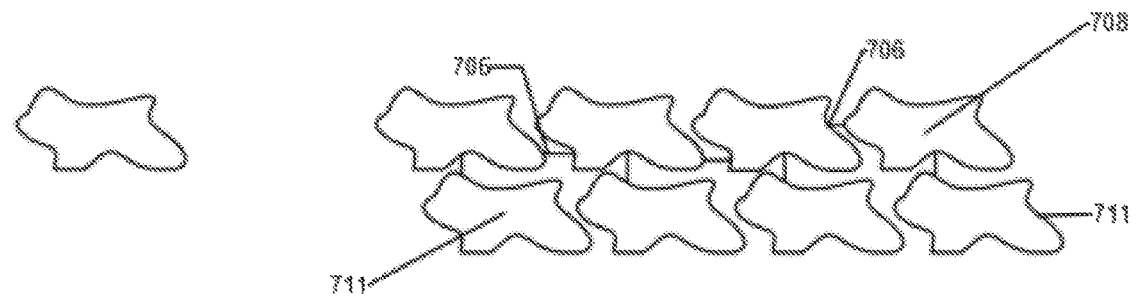
Figure 9E:
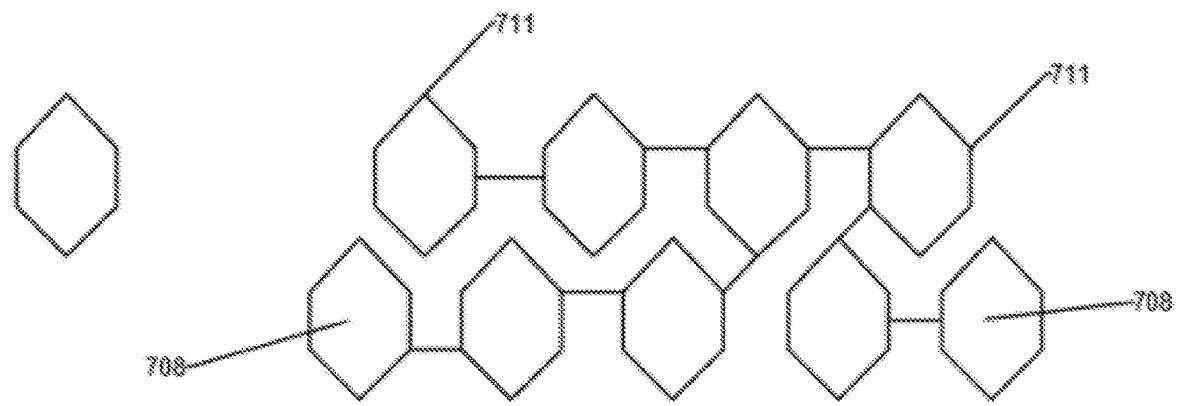

FIG. 8 illustrates the bioabsorbable stent system that comprise two bioabsorbable stents 802 and one bioabsorbable film 804. The bioabsorbable film 804 is coaxially sandwiched by two bioabsorbable stents 802.

Examples are shown in FIGS. 9A-E, a portion of the open cell hole 708 and the chamber 712 of the bioabsorbable stent is shown in a flattened condition so that the open cell hole 708 and the chamber 712 can be clearly viewed.

Figure 10:
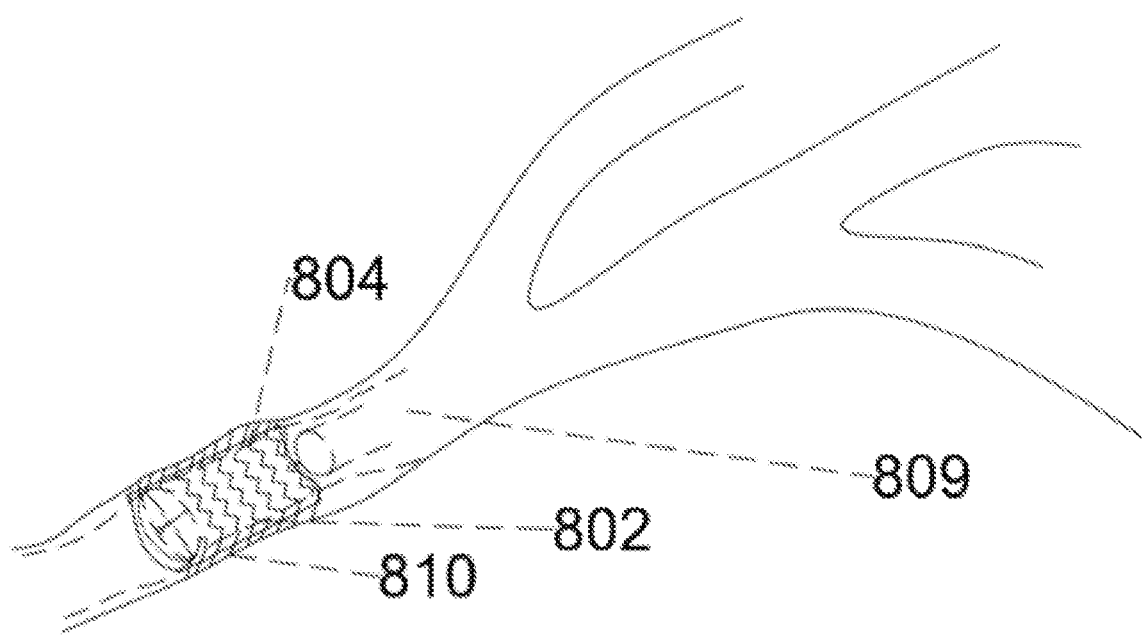
FIG. 10 shows an illustration of the bioabsorbable stent system after implantation in a stenoic body conduit.

FIG. 10 illustrates the bioabsorbable stent system after implantation in a stenoic body conduit 809. The implanted bioabsorbable stent system will contact and sustain the wall of vessel or natural or human-made body chamber.

Figure 11A:
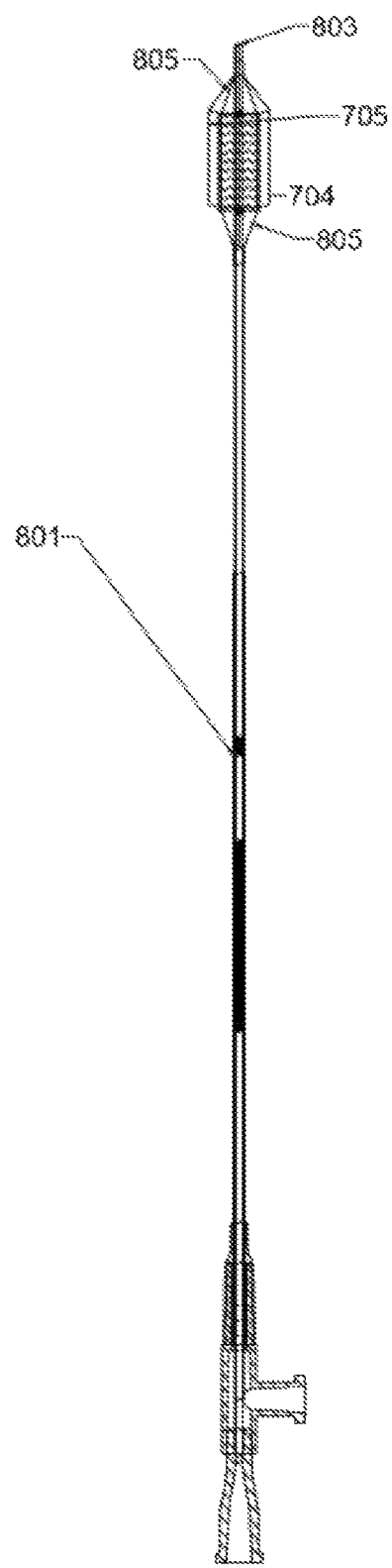
FIG. 11A is a structure illustration of the bioabsorbable stent system after expansion.
Figure 11B:
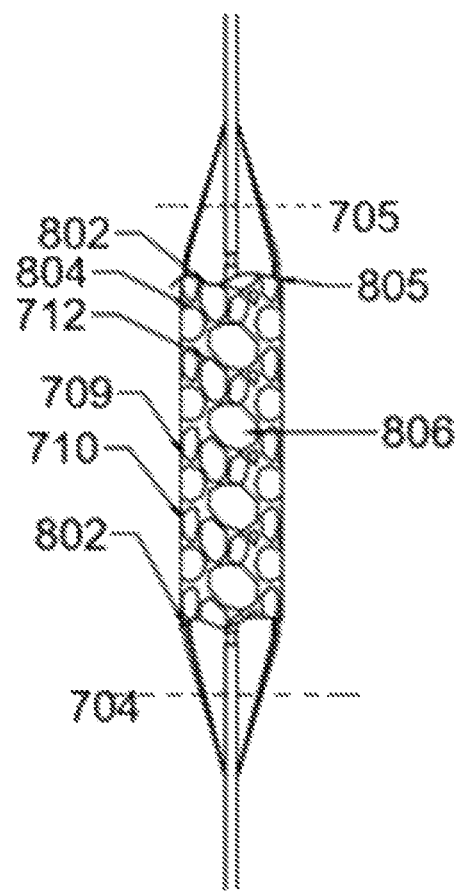
FIG. 11B is a structure illustration of partial enlarged detail of the bioabsorbable stent system after expansion.
Figure 11C:
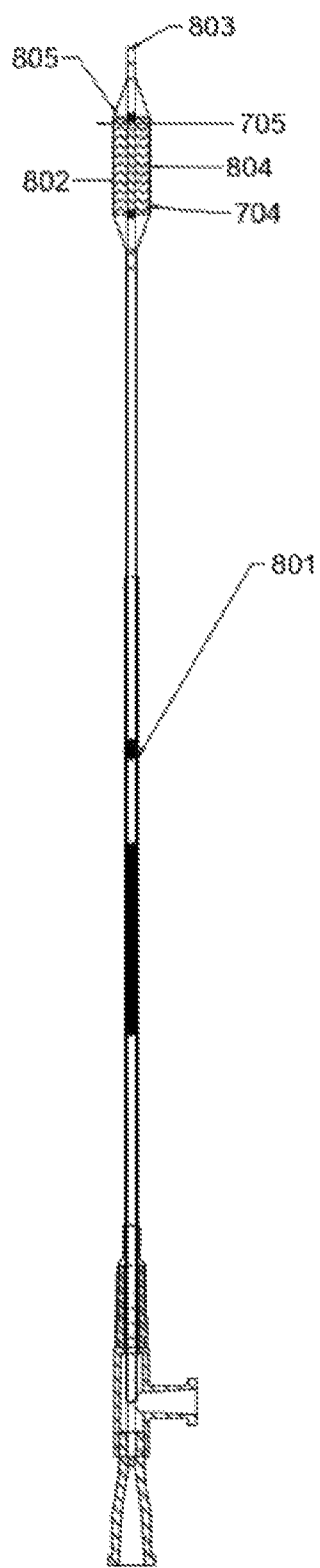
FIG. 11C is an illustration of the bioabsorbable stent system before crimping or compressing.

FIGS. 11A-C illustrate the bioabsorbable stent system loaded on a balloon catheter 801 before and after expansion. The bioabsorbable stent system that comprises bioabsorbable stents 802 and bioabsorbable film 804 is crimped on the balloon 805. There is typically a guide wire 803 to guide the balloon catheter 801 through to target position. Restoration agents may be cell growth factors or stem cells and its carrier, epithelial cells and its carrier, endothelial cells and its carrier.

The above examples illustrate technical conception and characteristics of this disclosure. While only a limited number of embodiments have been described, those skilled in the art, having benefit of this disclosure, will appreciate that other embodiments can be devised which do not depart from the scope of the disclosure. Other unsubstantial changes or modifications made to this application should be regarded as invasion on the scope of protection scope of this application.

What is claimed is:
1. A bioabsorbable stent system comprising one or more bioabsorbable stents and one or more restoration agents,
wherein a surface of the one or more bioabsorbable stents is coated with a first layer comprising cell growth factors suitable for a targeting position and a second layer comprising a drug suitable for the targeting position, wherein the one or more bioabsorbable stents is designed to first release the drug in the second layer, wherein following degradation of the second layer, the cell growth factors in the first layer are released, and wherein the cell growth factors are obtained from one or more of animal extraction, plant extraction, and artificial synthesis, and wherein the cell growth factors comprise one or more of platelet-related growth factors (PDGF, ODGF), epidermal growth factors (EGF, TGFα and TGFβ), insulin-like growth factor (IGF-I, IGF-II), nerve growth factor (NGF), interleukin growth factors (IL-1, IL-1, IL-3, etc.), erythropoietin (EPO), and colony stimulating factor (CSF).

2. The bioabsorbable stent system of claim 1, wherein the bioabsorbable stent comprises one or more bioabsorbable materials comprising one or more of magnesium, magnesium alloys, zinc alloy, iron, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

3. The bioabsorbable stent system of claim 1, wherein the bioabsorbable stent is manufactured by cutting, weaving, casting, molding, welding, and/or adhesive bonding.

4. The bioabsorbable stent system of claim 1, wherein a delivery system used to deliver the bioabsorbable stent system comprises a hollowing tubing, a push rod, a handler, a stent compressor, and/or a balloon catheter.

5. A bioabsorbable stent system comprising:
one or more bioabsorbable stents; and
one or more bioabsorbable films loaded with one or more restoration agents suitable for a targeting position,
wherein at least one bioabsorbable film is coaxially integrated inside the one or more bioabsorbable stents,
wherein at least one bioabsorbable film is an amniotic membrane,
wherein the one or more restoration agents comprises one or more of amniotic membrane, stem cells and a stem cell carrier, epithelial cells and an epithelial cell carrier, endothelial cells and an endothelial cell carrier, and cell growth factors,
wherein the one or more bioabsorbable stents is coated with a first layer comprising at least one restoration agent and a second layer comprising a drug suitable for the targeting position,
wherein the one or more bioabsorbable stents is designed to first release the drug in the second layer, and
wherein following degradation of the second layer, the at least one restoration agent in the first layer is released.

6. The bioabsorbable stent system according to claim 5, wherein the first layer is sandwiched between the bioabsorbable stent and the second layer.

7. The bioabsorbable stent system according to claim 5, wherein the bioabsorbable stent system comprises multiple coaxial bioabsorbable stents and wherein the one or more bioabsorbable films are loaded with restoration agents and are sandwiched between two adjacent coaxial bioabsorbable stents.

8. The bioabsorbable stent system according to claim 5, wherein the bioabsorbable stent system comprises a first layer of the bioabsorbable stent, a first layer of the bioabsorbable film, a second layer of bioabsorbable film and a second layer of the bioabsorbable stent sequentially from inside to outside of the bioabsorbable stent system, wherein the layers are coaxially integrated.

9. The bioabsorbable stent system according to claim 5, wherein the bioabsorbable stent system comprises a first layer of the bioabsorbable stent, a first layer of the bioabsorbable film, a second layer of bioabsorbable stent, a second layer of the bioabsorbable film, and a third layer of the bioabsorbable stent sequentially from inside to outside of the bioabsorbable stent system, wherein the layers are coaxially integrated.

10. The bioabsorbable stent system according to claim 5, wherein each of the stem cell carrier, the epithelial cell carrier, and the endothelial cell carrier comprises one or more of culture medium, a protein, peptide, and antibody.

11. The bioabsorbable stent system according to claim 5, wherein the one or more bioabsorbable films comprises one or more bioabsorbable materials comprising one or more of poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

12. The bioabsorbable stent system according to claim 5, wherein the one or more bioabsorbable stents comprises one or more bioabsorbable materials comprising one or more of magnesium, magnesium alloys, zinc alloy, iron, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

13. The bioabsorbable stent system according to claim 5, wherein the one or more bioabsorbable stents is manufactured by cutting, weaving, casting, molding, welding, and/or adhesive bonding.

14. The bioabsorbable stent system according to claim 5, wherein a coating on the surface of the one or more bioabsorbable stents comprises one or more bioabsorbable materials comprising one or more of poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

15. The bioabsorbable stent system according to claim 5, wherein the one or more bioabsorbable stents and the one or more bioabsorbable films are overlapped and coaxially jointed together through suturing, welding, co-molding, co-extrusion, adhesive bonding, solvent bonding or physically crimped and sandwiched by two adjacent bioabsorbable stents.

16. The bioabsorbable stent system according to claim 5, wherein the bioabsorbable stent system has a shape after expansion, wherein the shape is cylindrical, conical, frustum, or umbrella, and wherein the shape of the bioabsorbable stent system fits an implantation position of body conduits.

17. The bioabsorbable stent system according to claim 16, wherein the bioabsorbable stent system has a diameter of a proximal end and a diameter of a distal end, wherein the diameter of the proximal end is smaller than the diameter of the distal end when the shape of the bioabsorbable stent system is frustum.

18. The bioabsorbable stent system according to claim 5, wherein the drug comprises one or more of antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics ametastasis inhibitors, phytopharmaceuticals, chemotherapeutic agents, and amino acids.

19. The bioabsorbable stent system according to claim 5, wherein a delivery system used to deliver the bioabsorbable stent system comprises a hollowing tubing, a push rod, a handler, a stent compressor, and/or a balloon catheter.

* * * * *